United States Patent [19]

Nelson et al.

[11] Patent Number: 4,767,928
[45] Date of Patent: Aug. 30, 1988

[54] HIGH RESOLUTION BREAST IMAGING DEVICE UTILIZING NON-IONIZING RADIATION OF NARROW SPECTRAL BANDWIDTH

[76] Inventors: Robert S. Nelson, 25511 El Conejo La., Laguna Hills, Calif. 92653; Reuven D. Zach, 27572 Santa Clarita Rd., Saugus, Calif. 91350

[21] Appl. No.: 946,865

[22] Filed: Dec. 29, 1986

Related U.S. Application Data

[63] Continuation-in-part of Ser. No. 624,467, Aug. 27, 1984, Pat. No. 4,649,275.

[51] Int. Cl.⁴ ............................................. G01N 21/59
[52] U.S. Cl. .................................... 250/341; 128/664; 128/665; 250/339; 250/358.1; 250/360.1
[58] Field of Search .............. 378/154, 37; 250/360.1, 250/358.1, 341, 339; 128/665, 664

[56] References Cited

U.S. PATENT DOCUMENTS 4,360,885 11/1982 Edgar .................................. 364/525
4,515,165 5/1985 Carroll ................................ 128/664
4,649,275 3/1987 Nelson et al. .................... 250/358.1

FOREIGN PATENT DOCUMENTS 2452166 5/1976 Fed. Rep. of Germany ...... 378/154
0055193 5/1979 Japan .................................. 378/154

*Primary Examiner*—Janice A. Howell
*Assistant Examiner*—Constantine Hannaher
*Attorney, Agent, or Firm*—Lyon & Lyon

[57] ABSTRACT

The present invention provides a method and apparatus for high resolution breast imaging which uses collimated light (in the near ultraviolet, visible, or infrared) of a narrow spectral bandwidth rather than ionizing X-ray radiation. The collimated light is transmitted through the breast, losing intensity due to the reflective, absorptive and refractive properties of the breast materials in the beam path. Normal and diseased breast materials may exhibit distinctive characteristics from each other when exposed to different wavelengths of light. Several images can be acquired at distinct wavelengths of light to help differentiate normal and diseased breast materials. Light transmitted through the breast is recorded by a photodetector, generating an analog signal which can then be digitized and made available to a computer for analysis, processing and display. The light transmitted through the breast can be collimated to reduce the level of scattered light which reaches the photodetector, improving image quality.

11 Claims, 4 Drawing Sheets

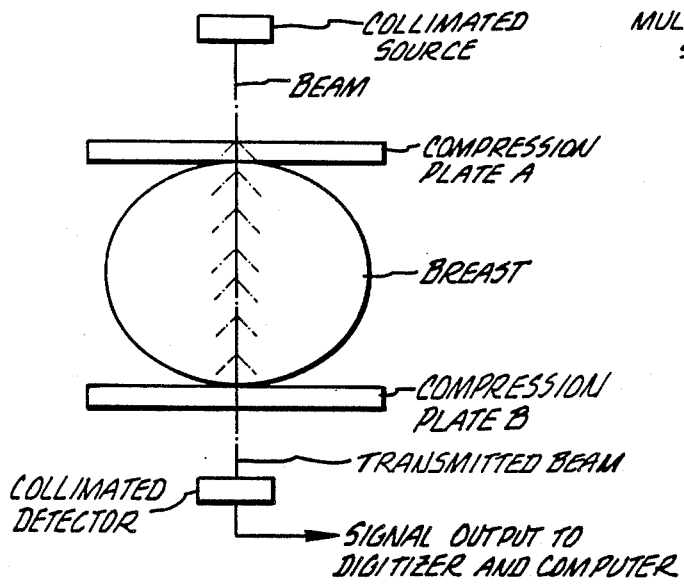
Fig. 2a.
RASTER SCAN FORMAT INCIDENT NORMAL TO SURFACE
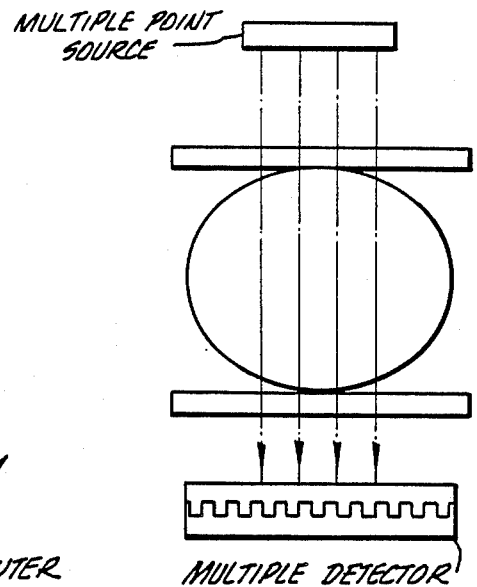
Fig. 2b.
MULTIPLE RASTER SCAN
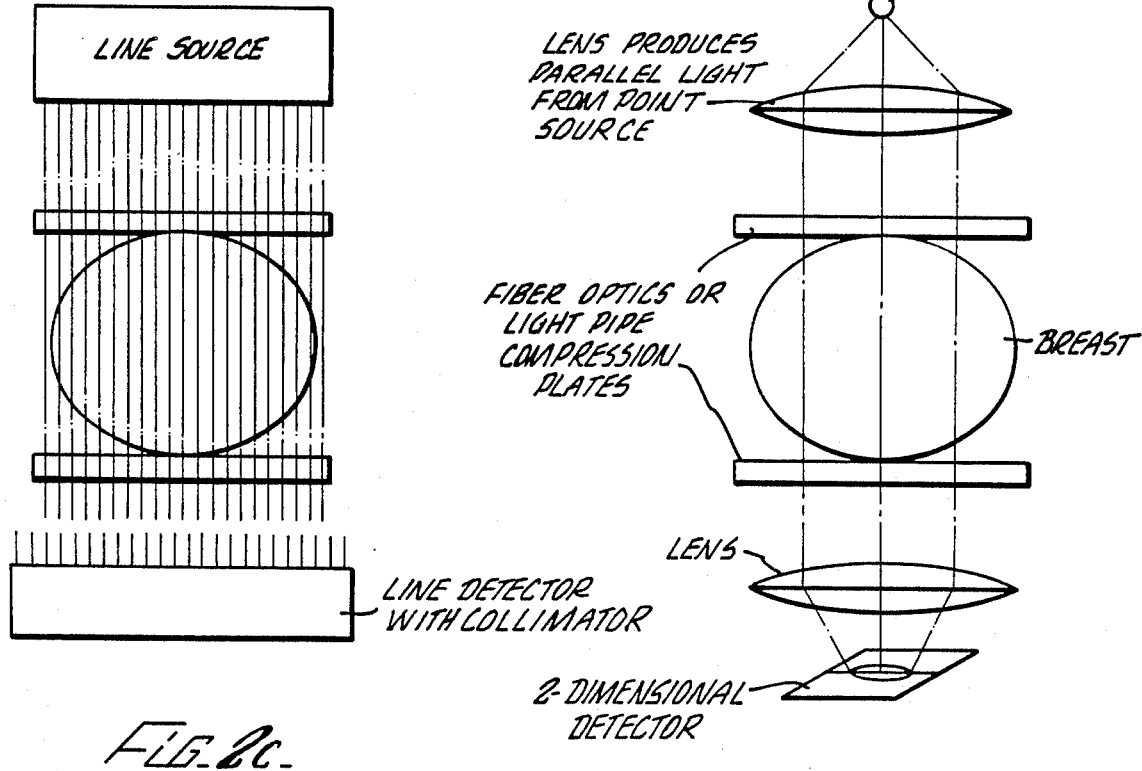
Fig. 2c.
Fig. 2d.

HIGH RESOLUTION BREAST IMAGING DEVICE UTILIZING NON-IONIZING RADIATION OF NARROW SPECTRAL BANDWIDTH

RELATED APPLICATION INFORMATION

This application is a continuation-in-part of application Ser. No. 624,467, filed Aug. 27, 1984, U.S. Pat. No. 4,649,275.

BACKGROUND OF THE INVENTION

X-ray mammography based on film-screen or Xeroradiographic detection is commonly accepted as a mass screening technique for breast disease. A certain risk is associated with this examination since X-ray radiation is also ionizing and dedicated X-ray equipment is often required.

More recently, broad beam light sources (sometimes referred to as "light torches") with a wide spectral bandwidth in the visible and infrared have been used to examine the breast. The broad beam transmitted through the breast is usually recorded by a video camera, converted to an analog signal and viewed on a video monitor or digitized and analyzed on a computer. The ability to discriminate between various tissue-types in the breast is poor due to the wide spectral bandwidth of the transmitted beam. Resolution is lost since a large amount of scattered light is transmitted from the breast to the detector.

Lesion sizes that are detectable with this approach have generally been no smaller than what the physician can detect by palpitation. Resolution is far below that which can be obtained with X-ray imaging systems.

We realize that a collimated light source of narrow spectral bandwidth (such as generated by a Laser) could be used to produce a beam or a number of beams of very small spatial dimensions. The small spatial dimensions of the beam could be used to obtain images of the breast with high spatial resolution, whereas the narrow spectral bandwidth would improve the characterization of the composition of the breast material being imaged to be more detailed. More information could be obtained by acquiring additional images at other wavelengths of light again, with narrow spectral bandwidths.

Although not essential to the invention disclosed, a desireable imaging format would be to have the collimated light beam(s) incident normal to the surface of the breast and to exit from the breast normal to the breast surface. The breast could be placed between two transparent plates and compressed so as to establish good surface contact and at the same time reducing the path length through the breast of the transmitted light beam(s). The compression technique is commonly employed in X-ray mammography.

The light entering and exiting from the plate-breast-plate system could undergo additional collimation so as to reject much of the scatter component. Collimation can be accomplished through use of masks, as for example of the checkerboard type. The whole object is imaged by moving the mask such that all points to be imaged are scanned.

DESCRIPTION OF THE DRAWINGS

FIG. 2(a): A collimated pencil beam from a point source used in a raster format. The detector may use additional collimation to help minimize detection of scattered light. Collimation techniques for scatter reduction may include air gaps, fiber optics, light pipes or mechanical apertures.

FIG. 2(b): Multiple point beams used in a raster scan format to reduce image acquisition time.

FIG. 2(c): A collimated (single or multiple) line beam of light provides a line scanning format. The array of detectors would use some form of collimation to reduce detected light scatter from the subject.

FIG. 2(d): A two-dimensional, parallel light beam is used for rapid image acquisition by a two-dimensional detector. In this case the collimation is incorporated into the compression plate(s).

DESCRIPTION OF THE INVENTION

A method and apparatus are described for mammographic (breast imaging) applications which entail using collimated light of narrow spectral bandwidth (near Ultraviolet, Visible and Infrared) to obtain high resolution images instead of ionizing radiation (X-rays).

Resolution can be controlled by adjusting the cross-sectional area of light beam(s) before and/or after transmission through the breast. Intense, narrow spectral bandwidth sources of light appropriate for this invention include lasers or filtered light sources.

The intensity of a light beam will be reduced by absorption, reflection and refraction as it is transmitted through the breast. These optical attributes of the various normal and diseased breast materials may exhibit wavelength dependence. Thus acquiring images at different wavelengths of light may aid in distinguishing tissue types or calcifications.

The transmitted light which is recorded by a detector represent the attenuated beam plus scattered light. Collimation can be introduced before the photodetector to reduce the level of this scattered light. The photodetector produces an analog signal which can be displayed or digitized for storage and analysis on a computer.

Figure 1A:
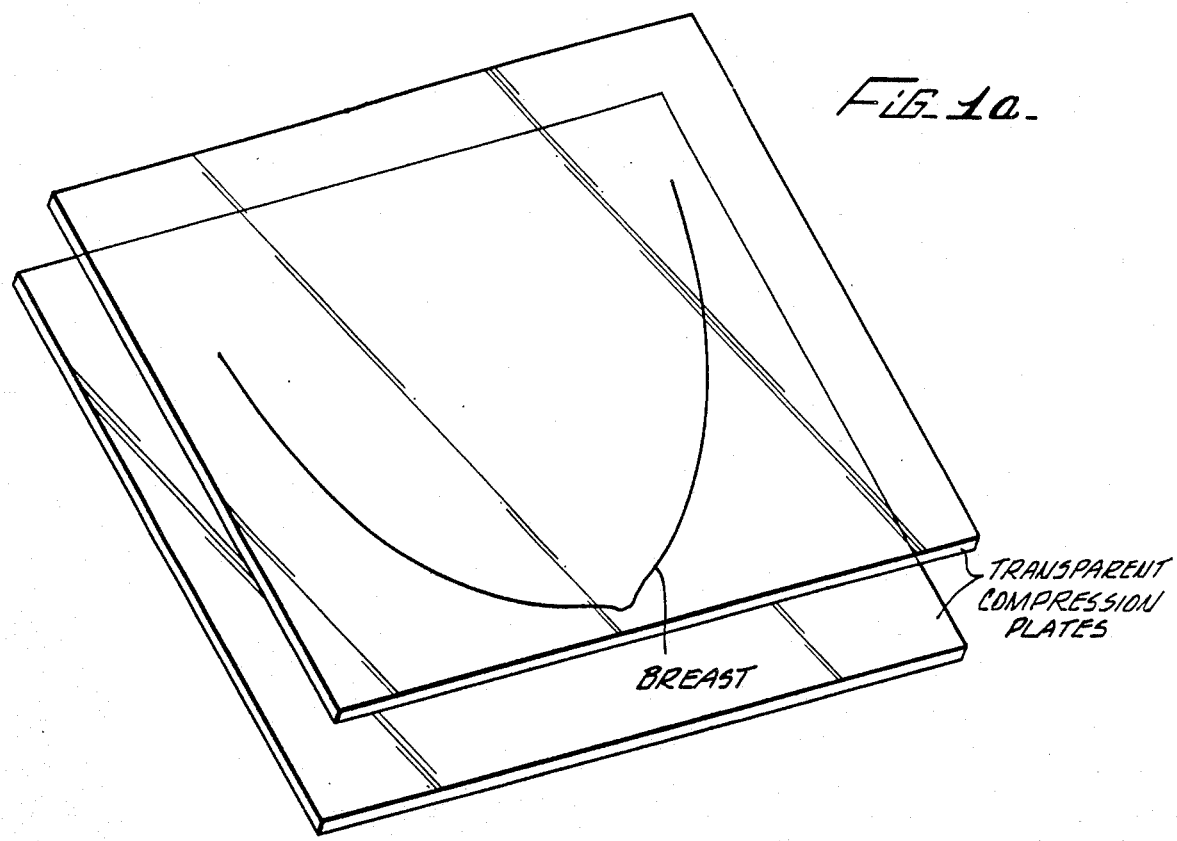
FIG. 1(a): A breast is shown in a compressed position between two transparent plates. These "compression" plates are transparent to the light wavelengths which would be used in imaging the breast. For illustrative purposes, the size of these plates is similar to those used in conventional X-ray mammography. Plate size can be reduced to permit imaging of small sections of a breast.
Figure 1B:
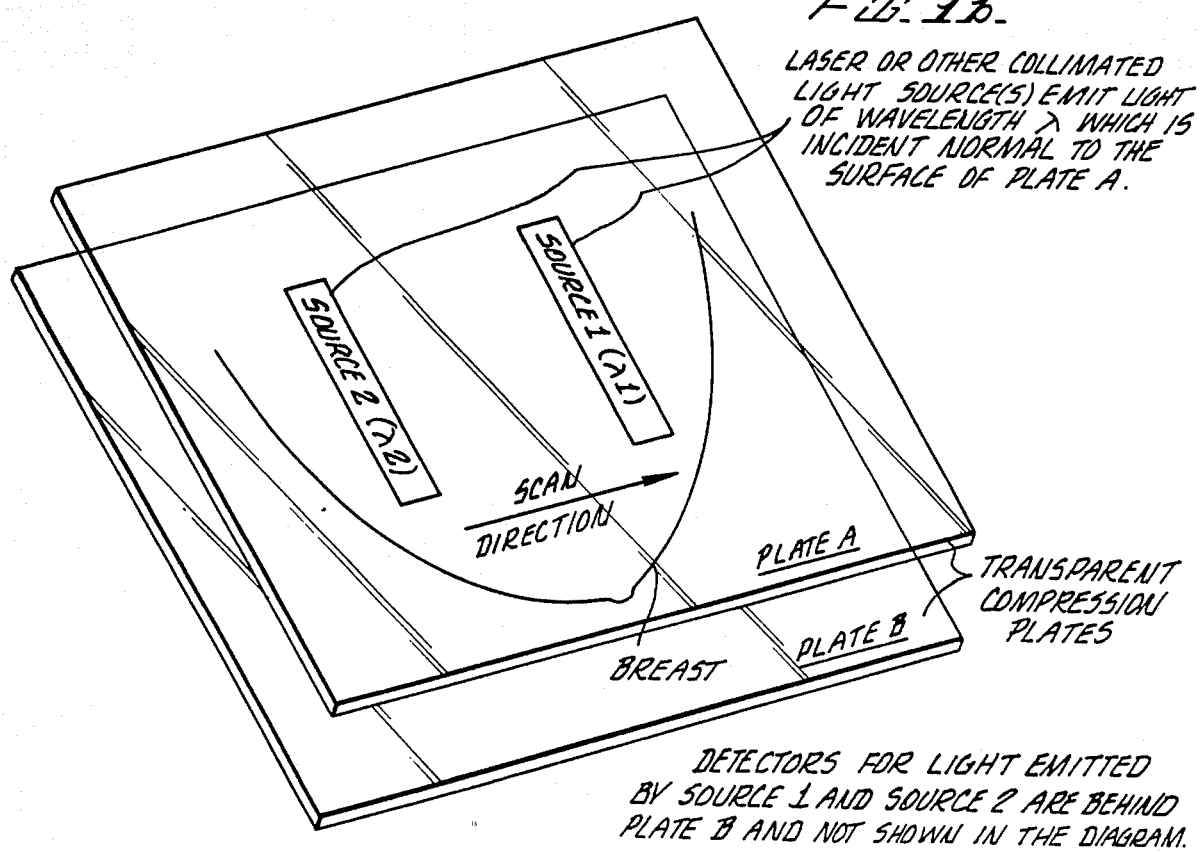
FIG. 1(b): One, two or more point, line, or two-dimensional sources, each source emitting collimated light of a distinct wavelength is (are) moved parallel to the surface of a compression plate. A detector corresponding to each source moves in synchronism with the source parallel to the surface of the second plate. Analog signals from the detector(s) can be digitized and stored in computer memory for display, processing and analysis purposes.

The breast often has an irregular shape. To reduce any problems associated with light incident on and transmitted out of surfaces which are not necessarily normal to the direction of beam transmission, it is desirable to flatten the entrance and exit breast surfaces. This is easily accomplished using a pair of transparent, flat plates [see FIG. 1(a)]. As can be appreciated from FIG. 1(b), a light beam of wavelength λ1 sent from source 1 is incident normal to the surface of one compression plate. The transmitted light is attenuated by the two plates and the breast material. An image or images can be acquired by simultaneously translating one or more light source light detector combination past the breast. Each light source emits a different wavelength (λ1≠λ2) as shown in FIG. 1(b).

High resolution images may be obtained with a variety of scanning techniques: FIGS. 2(a, b) show a point beam or multiple point beam which could be used in a raster scan format. The transmitted light beam can be collimated by a simple air gap, fiber-optics, light-pipes or mechanical aperture to minimize detection of scattered light. This approach can be extended to include a single line or multiple line scan format as shown in FIG. 2(c).

High speed two dimensional imaging is shown in FIG. 2(d). In this case collimation (such as fiber-optics or light pipes) can be introduced into one or both compression plates.

In all cases collimation may be used to produce a beam or beams of very small cross-section and a highly directional nature. This latter attribute can be used to exclude transmitted scatter from the exit beam.

Since many versions of this invention are possible, light sources requirements may range from a continuous to a rapidly pulsed source.

Figure 3:
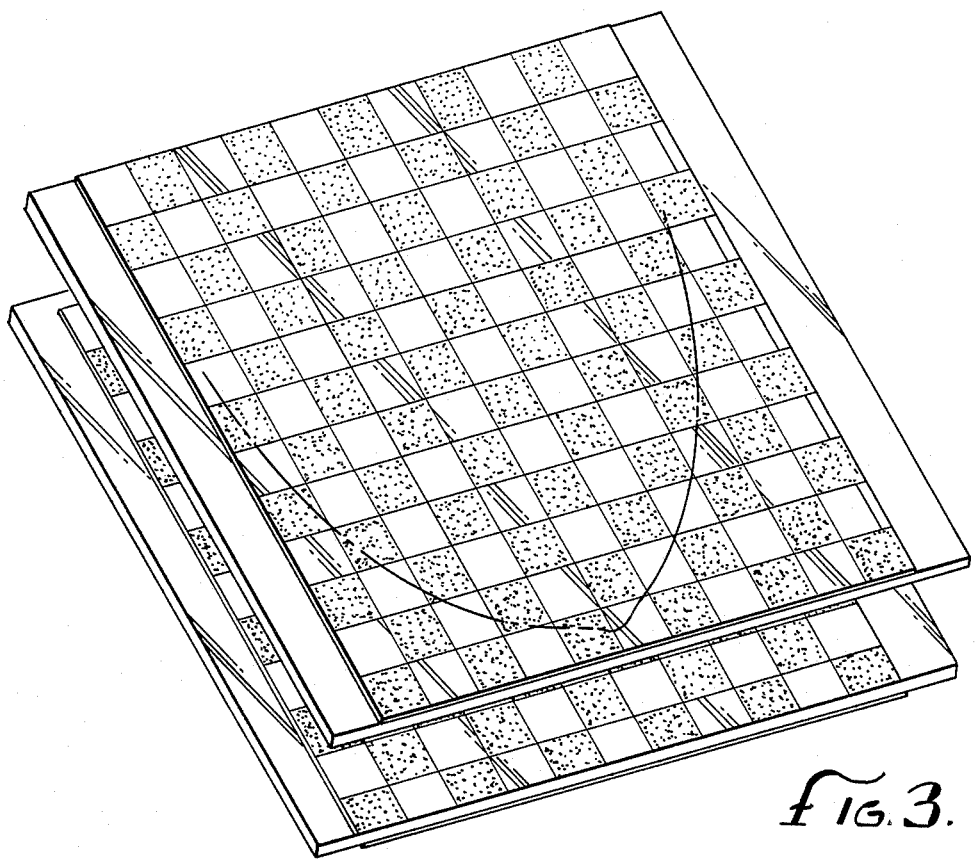
FIG. 3 shows a patterned mask of the checkerboard-type for use as a collimator.

Collimation to reduce the detected intensity of scattered light can be achieved through use of masks or virtual masks. A checkerboard pattern, as shown by way of example in FIG. 3, may be used. In one embodiment the checkerboard mask would be interposed between the source and the breast. Radiation from a source, as for example a line source or a 2-dimensional source, is blocked partially by the opaque portions of the checkerboard mask prior to transmission through the breast. Use of the mask results in a reduction of detected intensity from scattered radiation since the multiple sources created by the mask are now spatially separated. The complete object to be imaged is scanned by moving the checkerboard mask by one square, such that a region which had previously been covered by an opaque region is now covered by a transparent region, and vice versa. Optionally, an identical mask aligned with the mask may be used after the breast to further limit detected scatter. Mask patterns other than a checkerboard may be used, for example, with hexagonal-shaped transparent and opaque regions.

Figure 4:
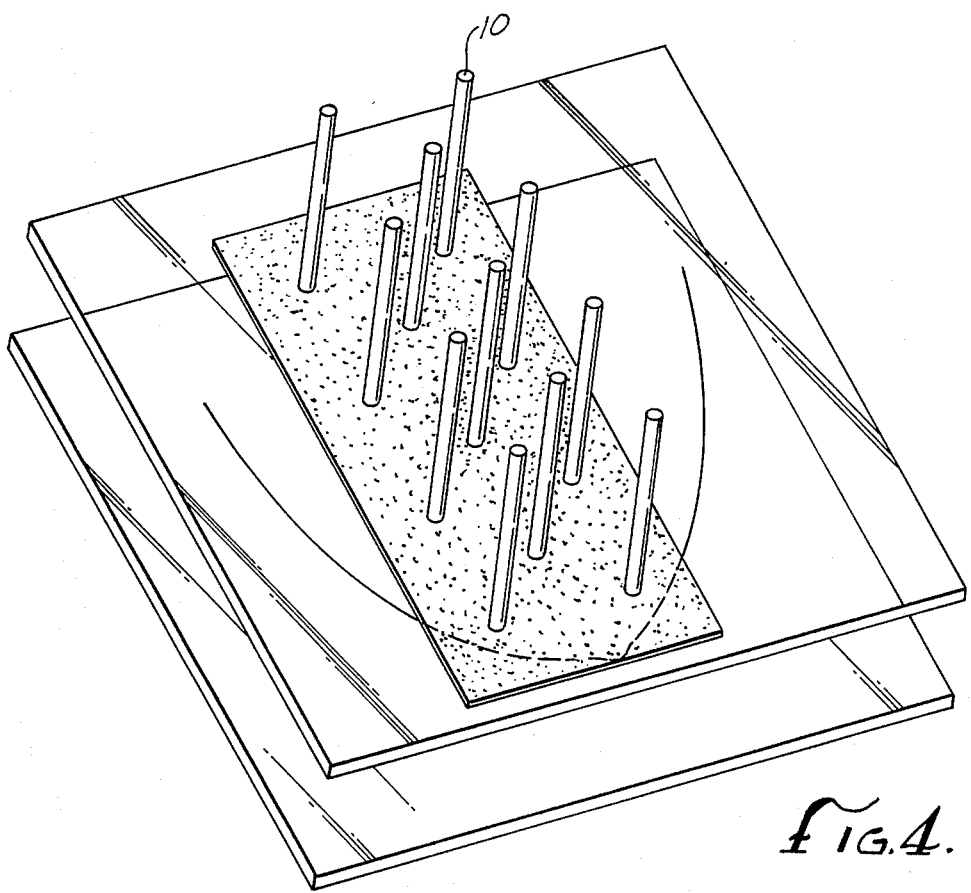
FIG. 4 shows construction of a virtual mask comprised of a matrix of fiber optic pipes which are spaced apart.

Virtual masks may also be employed. Such a virtual mask is shown by way of example in FIG. 4. Sources 10 are spaced apart such as to transmit radiation at locations less than covering the whole field. The sources 10 may be light pipes, which are then spaced apart from each other. Other types of sources may be used. An image is acquired by moving the virtual mask to new locations until all points have been scanned.

Figure 5:
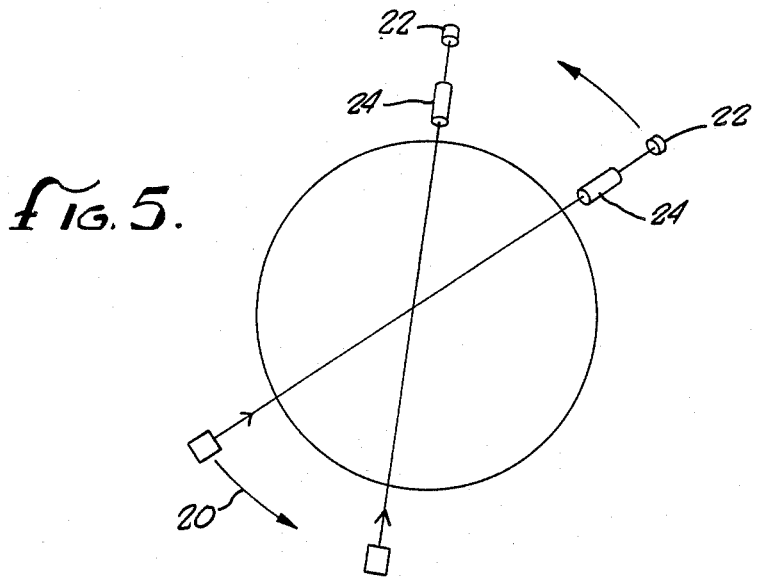
FIG. 5 shows an on axis view of the use of collimators in an optical computed tomography arrangement.

Imaging of the breast with optical methods may be accomplished by techniques described elsewhere. See, e.g., U.S. Pat. No. 4,515,165, issued May 7, 1985 to Carroll. the techniques of this invention may be beneficially employed in optical computed tomography. ("optical tomography"). As shown in FIG. 5, the basic arrangement utilized in optical tomography is to place a radiation source 20 on one side of the breast or object to be scanned, and the detector 22 on the other side. A collimator 24 is disposed in the beam path such that scattered radiation is reduced prior to the detector 22. The source 20, detector 22 and collimator 24 are moved relative to the object to be scanned such that sufficient information can be detected such that a tomographic image can be computed.

Figure 6:
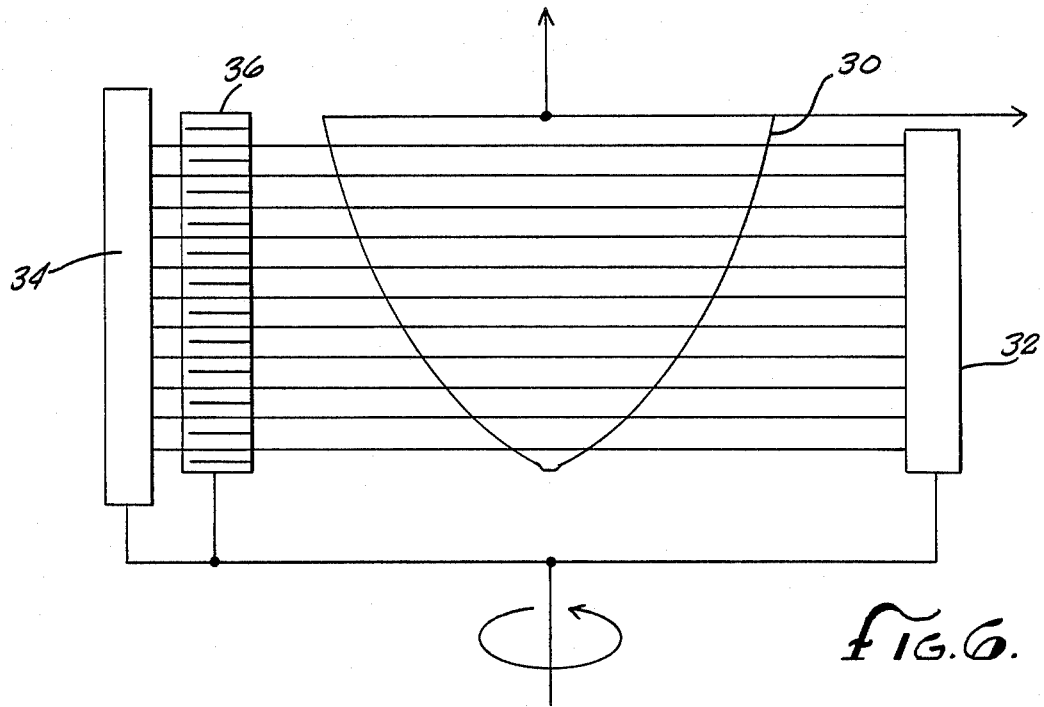
FIG. 6 shows a cross-sectional view of the use of collimators in optical computer tomography.
Figure 7:
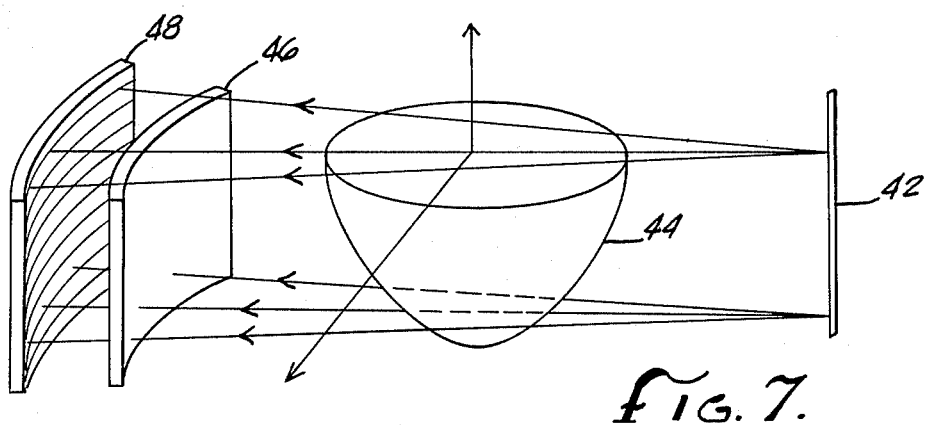
FIG. 7 shows a perspective view of a multiple fan beam scanning arrangement in optical computed tomography.

It will be appreciated that optical tomograph utilizing a collimator can be employed in a variety of fashions. As shown in FIG. 6, an object, such as a breast 30 may be imaged by a source of radiation 32 generating a one or two dimensional source of radiation, a detector 34 and a collimator 36 disposed between the source 32 and the detector 34. In this way multiple two dimensional images may be obtained simultaneously, thereby providing a three dimensional image of the object. As shown in FIG. 7, a line source 42 or linear array of point sources may irradiate the object to be scanned such as a breast 44, the transmitted radiation then passing through a collimator 46, and then being detected by a detector 48, such as a two dimensional array of detectors, or a camera.

Though the invention has been described with respect to a specific preferred embodiment thereof, many variations and modifications will immediately become apparent to those skilled in the art. It is therefore the intention that the appended claims be interpreted as broadly as possible in view of the prior art to include all such variations and modifications.

What is claimed is:

1. An apparatus for obtaining mammography images using non-ionizing radiation including:
   a source of non-ionizing radiation of relatively narrow bandwidth disposed such that the radiation will be incident on the breast,
   an optical detector disposed so as to detect the radiation after having passed through the breast, and
   one or more tasks for reducing the detected intensity of radiation scattered by the breast disposed between the source of non-iodizing radiation and the optical detector.

2. The apparatus of claim 1 wherein the mask for reducing the detected intensity of radiation scattered by the breast is a checkerboard pattern.

3. The apparatus of claim 1 wherein the mask for reducing the detected intensity of radiation scattered by the breast is a virtual mask.

4. The apparatus of claim 3 wherein the virtual mask is composed of an array of fiber optic light pipes.

5. A method for obtaining mammography images using non-iodizing radiation including:
   irradiating the breast with non-iodizing radiation of a relatively narrow bandwidth,
   transmitting the radiation through the breast,
   detecting the intensity of the radiation after it has passed through the breast, and
   reducing the detected intensity of radiation scattered by the breast by collimating the radiation by a mask prior to the detection step.

6. The method of claim 5 wherein the mask is a checkerboard pattern.

7. The method of claim 5 wherein the mask is a virtual mask.

8. The method of claim 7 wherein the virtual mask is composed of an array of fiber optic light pipes.

9. A method for obtaining mammography images using optical computed tomography including:

irradiating the breast with non-ionizing radiation of a relatively narrow bandwidth, transmitting the radiation through breast, detecting the intensity of the radiation after it has passed through the breast, and reducing the detected intensity of radiation scattered by the breast by collimating the radiation prior to the detection step by use of a mask.

10. An apparatus for obtaining mammography images via optical computed tomography using non-ionizing radiation including:

a source of non-ionizing radiation of relatively narrow bandwidth disposed such that the radiation will be incident on a breast, an optical detector disposed so as to detect the radiation after having passed through breast, and reducing the detected intensity of radiation scattered by the breast by disposing one or more masks between the source of non-ionizing radiation and the optical detector.

11. An apparatus for obtaining mammography images via optical computed tomography using non-ionizing radiation including:

a source of non-ionizing radiation of relatively narrow bandwidth disposed such that the radiation will be incident on a breast, an optical detector disposed so as to detect the radiation after having passed through breast, and means of collimation such as air gaps, fiber optics, light pipes or mechanical apertures so as to reduce the detected intensity of radiation scattered by the breast.

* * * * *

UNITED STATES PATENT AND TRADEMARK OFFICE
CERTIFICATE OF CORRECTION

PATENT NO. : 4,767,928

DATED : August 30, 1988

INVENTOR(S) : Robert S. Nelson and Reuven D. Zach

It is certified that error appears in the above—identified patent and that said Letters Patent is hereby corrected as shown below:

In claim 1, at column 4, line 39, "tasks" should be "masks".

Signed and Sealed this

Third Day of October, 1989

Attest:

DONALD J. QUIGG

*Attesting Officer*  *Commissioner of Patents and Trademarks*